(12) United States Patent
Samuels et al.

(10) Patent No.: US 9,134,249 B2
(45) Date of Patent: Sep. 15, 2015

(54) ELECTRIC FIELD GENERATING APPARATUS FOR PERFORMING SPECTROSCOPY

(71) Applicant: Hewlett-Packard Development Company, L.P., Houston, TX (US)

(72) Inventors: Brian C. Samuels, Fremont, CA (US); Zhiyong Li, Foster City, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 108 days.

(21) Appl. No.: 13/750,695

(22) Filed: Jan. 25, 2013

(65) Prior Publication Data

US 2014/0211196 A1    Jul. 31, 2014

(51) Int. Cl.
| | | |
|---|---|---|
| *G01N 21/00* | (2006.01) | |
| *G01N 21/55* | (2014.01) | |
| *G01J 3/44* | (2006.01) | |
| *G01N 21/65* | (2006.01) | |

(52) U.S. Cl.
CPC ......... *G01N 21/658* (2013.01); *Y10T 29/49155* (2015.01)

(58) Field of Classification Search
CPC .................. G01N 21/658; G01N 21/47; Y01T 29/49155; B82Y 25/00; G01J 3/44
USPC .......................................... 356/301, 445, 446
See application file for complete search history.

(56) References Cited

U.S. PATENT DOCUMENTS

| | | | |
|---|---|---|---|
| 6,770,488 B1 | 8/2004 | Carron et al. | |
| 8,129,676 B2 | 3/2012 | Vestel et al. | |
| 8,134,122 B2 | 3/2012 | Guharay | |
| 8,149,397 B2 | 4/2012 | Lee et al. | |
| 2003/0164947 A1* | 9/2003 | Vaupel | 356/445 |
| 2006/0072113 A1* | 4/2006 | Ran et al. | 356/445 |
| 2007/0295208 A1 | 12/2007 | Fairchild | |
| 2010/0210029 A1 | 8/2010 | Meinhart et al. | |
| 2012/0107948 A1* | 5/2012 | Li et al. | 436/149 |
| 2012/0164745 A1 | 6/2012 | Fu et al. | |
| 2012/0196304 A1 | 8/2012 | Dees et al. | |

OTHER PUBLICATIONS

Alvarez-Puebla, R.A. et al., Gold Nanorods 3d-supercrystals as Surface Enhanced Raman Scattering Spectroscopy Substrates for the Rapid Detection of Scrambled Prions, (Research Paper), Mar. 28, 2011.

* cited by examiner

*Primary Examiner* — Tarifur Chowdhury
*Assistant Examiner* — Sunghee Y Gray
(74) *Attorney, Agent, or Firm* — Mannava & Kang, P.C.

(57) ABSTRACT

According to an example, an apparatus for performing spectroscopy includes a substrate on which a plurality of surface-enhanced spectroscopy (SES) elements are positioned substantially along a first plane. The apparatus also includes a first electrode positioned adjacent to the plurality of SES elements substantially along the first plane and a second electrode positioned adjacent to the plurality of SES elements substantially along the first plane and on a side of the plurality of SES elements that is opposite the first electrode. The first electrode and the second electrode are to generate an electric field around the plurality of SES elements when voltages are applied through the first electrode and the second electrode.

12 Claims, 6 Drawing Sheets

ELECTRIC FIELD GENERATING APPARATUS FOR PERFORMING SPECTROSCOPY

BACKGROUND

In surface-enhanced spectroscopy (SES), such as surface-enhanced Raman spectroscopy (SERS), vibrationally excitable levels of an analyte are probed. The energy of a photon can shift by an amount equal to that of the vibrational level excited by the photon (Raman scattering). A Raman spectrum, which consists of a wavelength distribution of bands corresponding to molecular vibrations specific to the analyte being probed, may be detected to identify the analyte. In SERS, the analyte molecules are in close proximity, for instance, less than tens of nanometers, to metal nano-particles that may be or may not be coated with a dielectric, such as silicon dioxide, silicon nitride, and a polymer, that, once excited by light, set up plasmon modes (collective oscillations of free electron density), which create near fields around the metal nano-particles. These fields can couple to analyte molecules in the near field regions. As a result, concentration of the incident light occurs at close vicinity to the nano-particles, enhancing the emission of scattered signals from the analyte molecules.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1A:
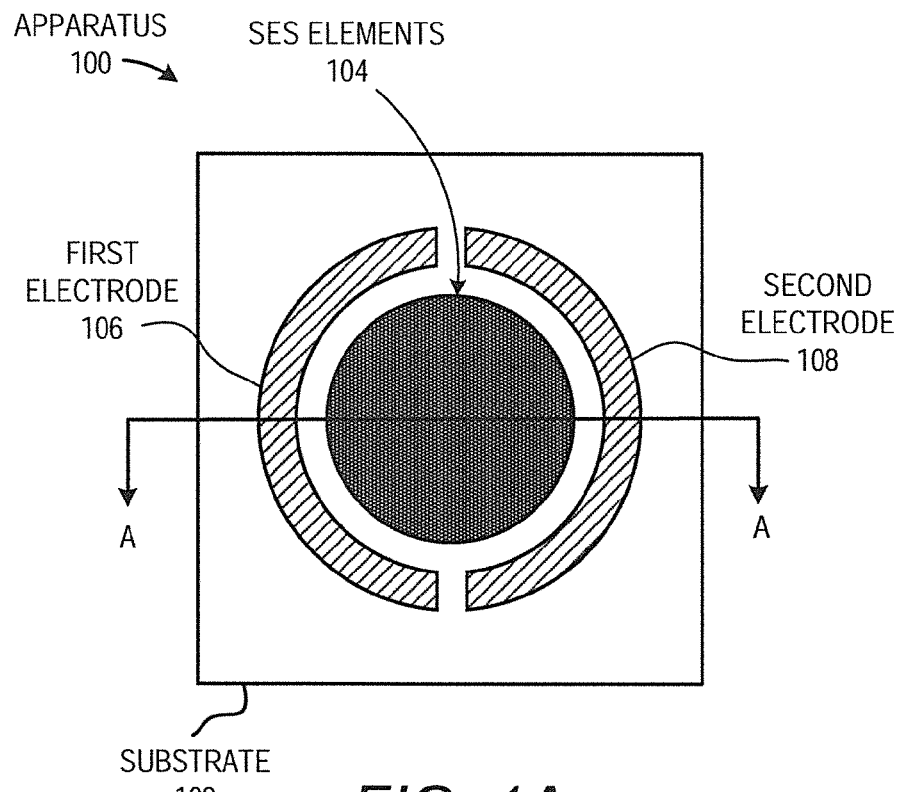
FIG. 1A shows a simplified top view of an apparatus for performing spectroscopy, according to an example of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared, near infrared, and ultra-violet portions of the electromagnetic spectrum.

Disclosed herein are apparatuses for performing spectroscopy, systems for performing spectroscopy, methods for fabricating an apparatus, and methods for using an apparatus for performing spectroscopy. The apparatuses disclosed herein may include a substrate having a surface and a plurality of surface-enhanced spectroscopy (SES) elements extending substantially along a first plane on the surface of the substrate. The apparatuses may also include a first electrode positioned adjacent to the plurality of SES elements substantially along the first plane and a second electrode positioned adjacent to the plurality of SES elements substantially along the first plane and on a side of the plurality of SES elements that is opposite the first electrode. The first electrode and the second electrode may generate an electric field around the plurality of SES elements when voltages are applied through the first electrode and the second electrode.

According to an example, when the apparatuses disclosed herein are positioned in a path of flow of a fluid containing ionized or polarized target particles, the electric field generated around the plurality of SES elements may cause some or all of the target particles to be steered toward the SES elements. The steering of the target particles toward the SES elements may generally increase the likelihood that the target particles will either contact or come into sufficiently close proximity to the SES elements for spectroscopy enhancement to occur, which increases the probability that the target particles will be detected through an SES operation. According to another example, the first electrode and the second electrode may be formed on the same substrate as the SES elements, which may result in a relatively simpler fabrication process of the apparatus disclosed herein as compared with other types of apparatuses for performing SES that typically form electrodes on multiple vertical layers.

With reference first to FIG. 1A, there is shown a simplified top view of an apparatus 100 for performing spectroscopy, according to an example. It should be understood that the apparatus 100 depicted in FIG. 1A may include additional components and that some of the components described herein may be removed and/or modified without departing from a scope of the apparatus 100. It should also be understood that the components depicted in FIG. 1A are not drawn to scale and thus, the components may have different relative sizes with respect to each other than as shown therein.

The apparatus 100 may be implemented to perform spectroscopy, which may include surface-enhanced Raman spectroscopy (SERS), surface-enhanced luminescence detection, surface-enhanced fluorescence detection, or other types of surface-enhanced optically enhanced detection. The apparatus 100 may include a substrate 102, a plurality of surface-enhanced spectroscopy (SES) elements 104, a first electrode 106, and a second electrode 108. In addition, the first electrode 106 may be positioned adjacent to one side of the plurality of SES elements 104 and the second electrode 108 may be positioned adjacent to another side of the plurality of SES elements 104, in which the second electrode 108 may be positioned on an opposite side of the plurality of SES elements 104 as compared with the first electrode 106.

It should be understood that the depiction of the apparatus 100 is for purposes of illustration and that various modifications to the components of the apparatus 100 may be made without departing from a scope of the apparatus 100. For instance, the plurality of SES elements 104 may be arranged in alternate configurations, such as, a polygon shape, an oval shape, etc. As another example, the first electrode 106 and the second electrode 108 may have shapes other than the "C" or semi-circular shapes depicted in FIG. 1A. For instance, the first electrode 106 and/or the second electrode 108 may be broken up in to multiple segments. In addition, or alternatively, the first electrode 106 and/or the second electrode 108 may have a linear configuration.

Figure 1B:
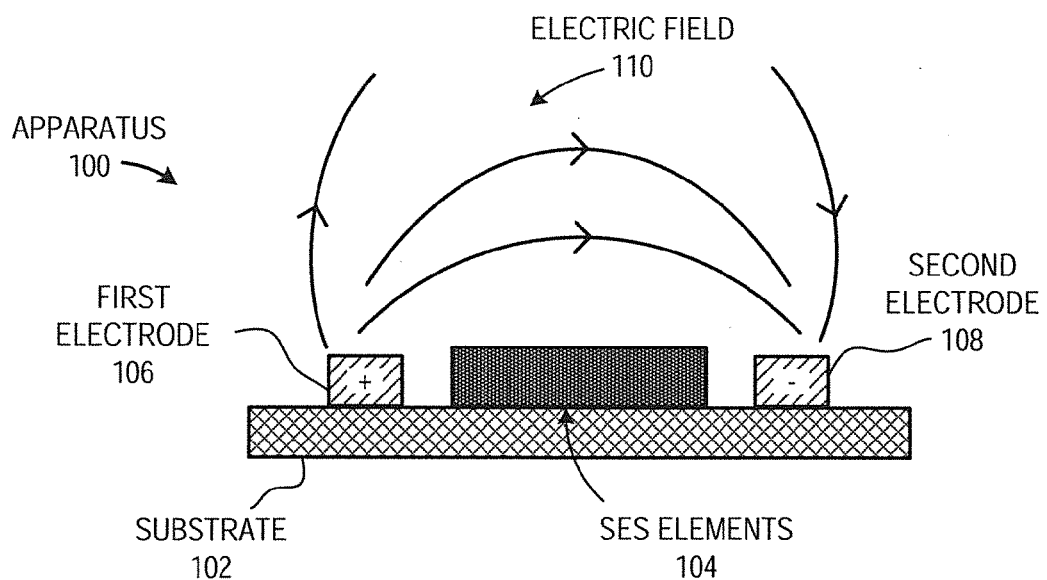
FIG. 1B shows a cross-sectional side view of the apparatus depicted in FIG. 1A taken along lines A-A, according to an example of the present disclosure.

Turning now to FIG. 1B, there is shown a cross-sectional side view of the apparatus 100 taken along lines A-A in FIG. 1A, according to an example. As shown in FIG. 1B, the SES elements 104 extend substantially along a plane on the surface of the substrate 102. In addition, the first electrode 106 may be positioned adjacent to the SES elements 104 and the second electrode 108 may be positioned adjacent to the SES elements 104, but on an opposite side of the SES elements 104. The first electrode 106 and the second electrode 108 may be positioned substantially along the plane at which the SES elements 104 extend along the surface of the substrate 102. In the example depicted in FIG. 1B, the first electrode 106 and the second electrode 108 may also be positioned on the substrate 102. In one regard, therefore, the first electrode 106 and the second electrode 108 may be fabricated on the same substrate 102 as the SES elements 104, which may simplify fabrication of the apparatus 102 as compared with apparatuses that require vertically arranged electrodes.

Although not shown in FIG. 1B, the first electrode 106 and the second electrode 108 may be connected to a voltage source that is to apply a current having a first bias through the first electrode 106 and a current having a second bias through the second electrode 108. By way of example, the first electrode 106 and the second electrode 108 may be connected to the voltage source or multiple voltage sources through a connection or connections (e.g., a wire or wires) that is/are positioned through the substrate 102. In FIG. 1B, the first electrode 106 may have a positively (+) biased voltage supplied therethrough and the second electrode 108 may have a negatively (−) biased voltage supplied therethrough. In another example, an AC biased voltage with various frequencies may be applied to the first electrode 106 and the second electrode 108. The application of the voltages through the first electrode 106 and the second electrode 108 may also generate an electric field 110. The electric field 110 may be formed above the plurality of SES elements 104. As discussed in greater detail herein, the electric field 110 generated between the first electrode 106 and the second electrode 108 may cause ionized or polarized particles to be steered toward the plurality of SES elements 104.

Generally speaking, the SES elements 104 may include elements that enhance the emission of any of light, fluorescence, luminescence, etc., by particles in contact with and/or in relatively close proximities to the SES elements 104 and therefore enhance sensing operations, such as surface enhanced Raman spectroscopy (SERS), enhanced photoluminescence, enhanced fluorescence, etc., on the particles. The SES elements 104 may include plasmonic nanoparticles or nanostructures, which may include plasmon-supporting materials such as but not limited to, gold (Au), silver (Ag), and copper (Cu). The SES elements 104 may also include structures arranged in various ordered or random configurations on substrates.

The SES 104 elements may have nanoscale surface roughness, which may generally be characterized by nanoscale surface features on the surface of the layer(s) and may be produced spontaneously during deposition of the plasmon-supporting material layer(s). By definition herein, a plasmon-supporting material is a material that facilitates scattering of signals and the production or emission of a signal from an analyte on or near the material during spectroscopy.

In some examples, the SES elements 104 may be functionalized to facilitate adsorption of analyte molecules. For example, surfaces of the SES elements 104 may be functionalized such that a particular class of analytes is attracted and may bond or be preferentially adsorbed onto the SES elements 104. Various manners in which the SES elements 104 may operate to enhance scattered light emissions from analyte molecules are described in greater detail herein below.

The apparatus 100 may include a relatively large number of SES elements 104 to substantially increase the enhancement of signal emissions (e.g., Raman scattered light, luminescence, fluorescence, etc.) from an analyte. In addition, the plurality of SES elements 104 may include any suitable dimensions that are sufficient for the SES elements 104 to substantially enhance the signal emissions and for a detector to detect the emitted signals. By way of particular example, the plurality of SES elements 104 extends across an area of any size between about 1 micron to 1 mm.

The first electrode 106 and the second electrode 108 may be formed of any suitable electrically conductive but electrochemically stable material under various operation conditions. In this regard, the first electrode 106 and the second electrode 108 may be formed of platinum (Pt), gold (Au), silver (Ag), copper (Cu), combinations thereof, etc. In addition, the first electrode 106 and the second electrode 108 may include any suitable dimensions and may be positioned in sufficiently close proximities to the SES elements 104 that enable the electrodes 106 and 108 to generate electric fields 110 around the plurality of SES elements 104 that are of sufficient strength to cause ionized or polarized particles to be directed toward the SES elements 104. The amount of voltage applied through the first electrode 106 and the second electrode 108 may also be controlled to generate an electric field having a sufficient strength to cause the ionized or polarized particles to be directed toward the SES elements 104.

The substrate 102 may be formed of any suitable material, such as, silicon, silicon nitride, glass, plastic, polymer, $SiO_2$, $Al_2O_3$, aluminum, etc., or a combination of these materials, etc.

Figure 2:
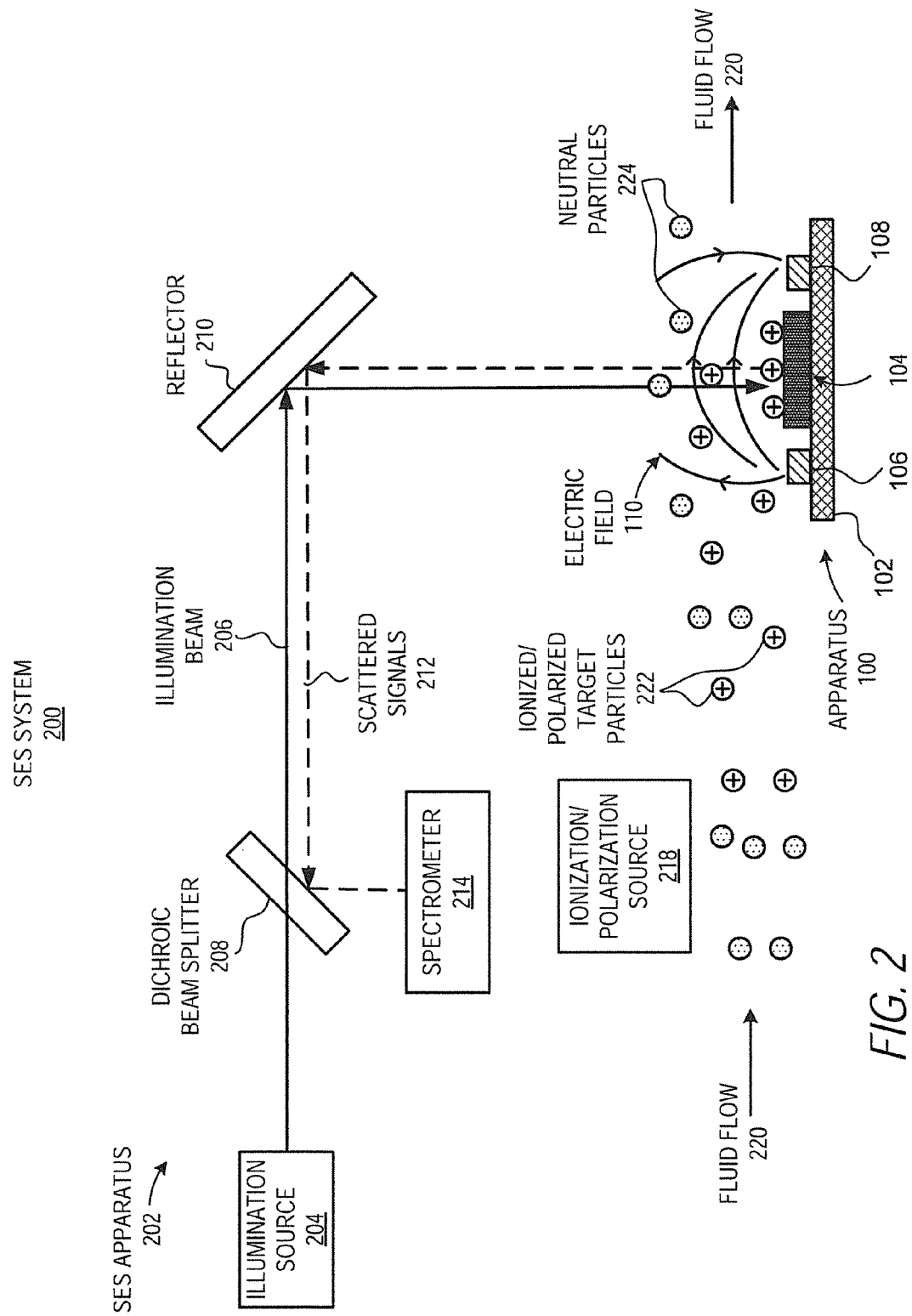
FIG. 2 shows a diagram of a SES system that includes a SES apparatus and an apparatus for performing SES, according to an example of the present disclosure.

Turning now to FIG. 2, there is shown a diagram of a SES system 200 that includes a SES apparatus 202 and an apparatus 100 for performing SES, according to an example. It should be understood that the SES system 200 depicted in FIG. 2 may include additional components and that some of the components described herein may be removed and/or modified without departing from a scope of the SES system 200. It should also be understood that the components depicted in FIG. 2 are not drawn to scale and thus, the components may have different relative sizes with respect to each other than as shown therein.

As shown in FIG. 2, the SES apparatus 202 may include an illumination source 204, a dichroic beam splitter 208, a reflector 210, and a spectrometer 214. The illumination source 204 may emit a beam of illumination 206 (such as a laser beam, an LED beam, or other type of light beam) through the dichroic beam splitter 208. The illumination beam 206 may also be reflected by the reflector 210 onto the apparatus 100. The illumination beam 206 may illuminate the SES elements 104 and target particles in relatively close proximities to and/or contacting the SES elements 104.

The analyte molecules may be contained in a fluid that flows over the SES elements 104. In FIG. 2, the analyte molecules are depicted as being contained in a fluid flow 220, which may be a gas and/or a liquid. By way of example, the fluid flow 220 may include target particles and a relatively neutral material, such as, air, nitrogen, helium, argon, etc. The fluid flow 220 is also depicted as passing an ionization source 218, which ionizes the target particles 222 contained in the fluid flow 220. The ionization source 218 may include one of a corona source, a radioactive source, an electrospray, etc., to ionize the target particles contained in the fluid flow 220. In addition, or alternatively, the target particles may be ionized or polarized through operation of additional electrodes as discussed herein.

As also shown in FIG. 2, some of the target particles 222 in the fluid flow 220 may become ionized or polarized, while other particles, such as the gas and/or liquid contained in the fluid flow 220 remain neutral 224. In addition, an electric field 110 generated through application of voltages of reverse biases through the first electrode 106 and the second electrode 108, may steer the ionized or polarized target particles 222 toward the SES elements 104. Moreover, some of the ionized or polarized target particles 222 may become deposited onto, and in some instances bind with some of, the SES elements 104. In one regard, therefore, the ionized or polarized target particles 222 may be positioned in contact with or in close proximities to the SES elements 104, which may increase the enhancement effects of the SES elements 104, thereby enhancing the probability of the ionized or polarized target particles 222 being accurately detected.

Generally speaking, the illumination beam 206 may operate as an excitation light on the SES elements 104, which causes near fields around the SES elements 104 to be created. The near fields around the SES elements 104 may couple to the ionized or polarized target particles 222 in the vicinities of the SES elements 104. The metallic nanoparticles (or other plasmonic structures) of the SES elements 104 may also act to enhance the signal emission process of the ionized or polarized target particles 222. As a result, scattered signals 212 (e.g., Raman scattered light, luminescence, fluorescence, etc.) may be emitted from the ionized or polarized target particles 222 and the emission of the scattered signals 212 may be enhanced by the SES elements 104. A portion of the scattered signals 212, which may be emitted in all directions from the ionized or polarized target particles 222 near the SES elements 104, may be emitted toward the reflector 210.

The scattered signals 212 may be reflected from the reflector 210 and directed back to the dichroic beam splitter 208. The dichroic beam splitter 208 may also reflect the scattered signals 212 toward the spectrometer 214. The spectrometer 214 may include optical elements, such as, slits, gratings, lenses, etc., that allow for the separation and measurement of different wavelengths of light. The spectrometer 214 may also include a detector, e.g., a photomultiplier tube (PMT), a charge-coupled device (CCD), a complementary metal-oxide-semiconductor (CMOS), etc., detector) to measure the intensities of the separated wavelength bands. The measured intensities of the separated wavelength bands may be used to identify the analyte.

Various modifications may be made to the SES apparatus 202 depicted in FIG. 2 without departing from a scope of the SES system 200. For instance, the reflector 210 may have a parabolic shape that is to focus the illumination beam 206 onto the SES elements 104 and/or to focus the scattered signals 212 onto the dichroic beam splitter 208. As a yet further example, various additional optical components, e.g., mirrors, prisms, optical fibers, etc., may be positioned to direct the illumination beam 206 on the SES elements 104 and/or the scattered signals 212 to the spectrometer 214.

Figure 3A:
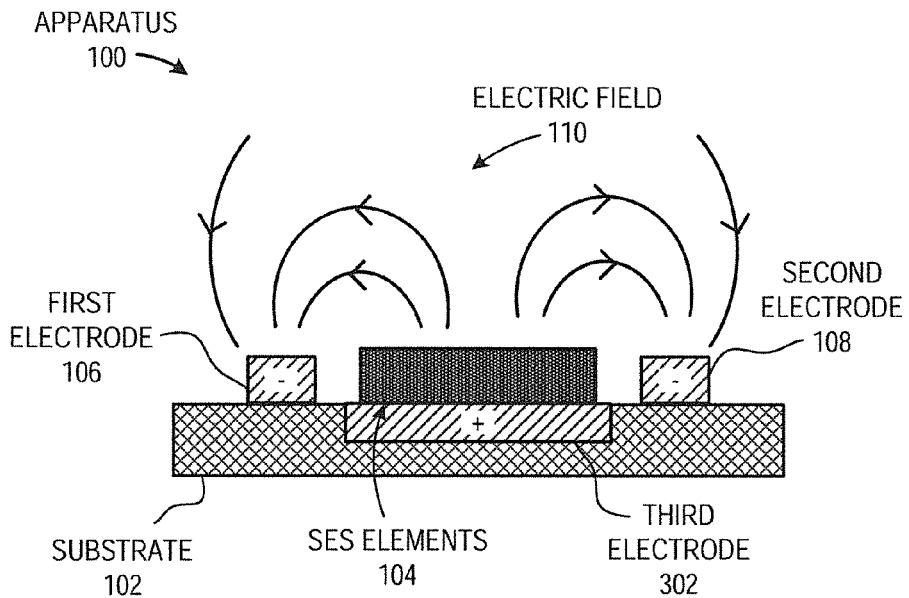
FIGS. 3A and 3B, respectively show cross-sectional side views of the apparatus depicted in FIG. 1B, according to two additional examples of the present disclosure.
Figure 3B:
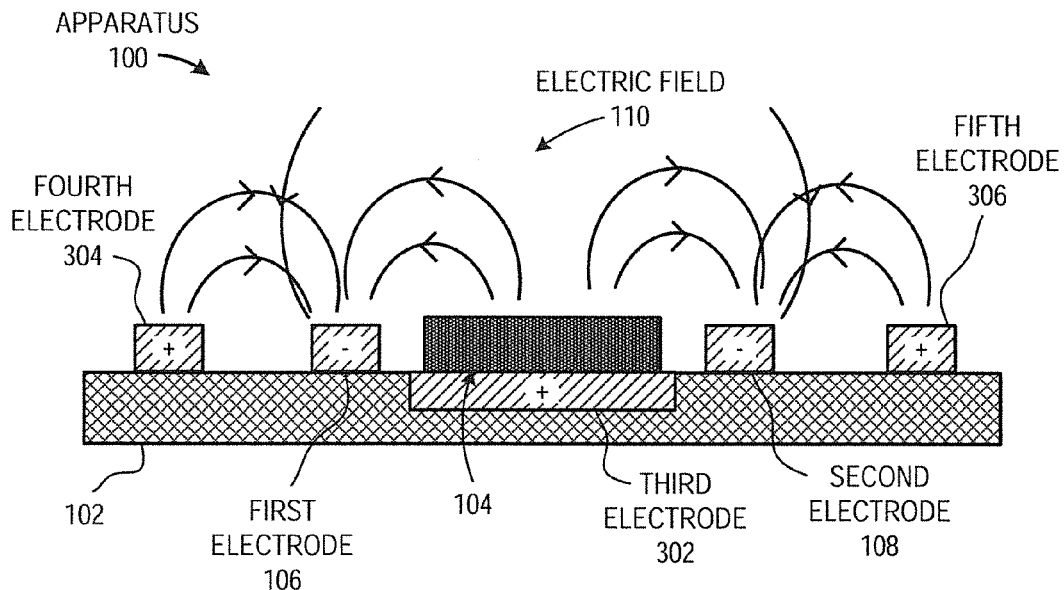

Turning now to FIGS. 3A and 3B, there are respectively shown cross-sectional side views of the apparatus 100 depicted in FIG. 1B, according to two additional examples. The apparatuses 100 depicted in FIGS. 3A and 3B may include similar features to those depicted in FIG. 1B and thus, common features will not be described again with respect to FIGS. 3A and 3B. The apparatus 100 depicted in FIG. 3A differs from the apparatus 100 depicted in FIG. 1B in that a third electrode 302 may be positioned in the substrate 102 beneath the plurality of SES elements 104. In addition, the first electrode 106 and the second electrode 108 may have the same bias and the third electrode 302 may have an opposite bias. As such, the electric field 110 generated by the first electrode 106, the second electrode 108, and the third electrode 302 in FIG. 3A may differ from the electric field 110 depicted as being generated in FIG. 1B.

The apparatus 100 depicted in FIG. 3B may include all of the features of the apparatus 100 depicted in FIG. 3A. In addition, the apparatus 100 depicted in FIG. 3B may also include a fourth electrode 304 and a fifth electrode 306. The fourth electrode 304 and the fifth electrode 306 may have any of the shapes and configurations of the first electrode 106 and the second electrode 108 discussed above. In addition, the fourth electrode 304 may be positioned outside of the first electrode 106 with respect to the plurality of SES elements 104. Moreover, the fifth electrode 306 may be positioned outside of the second electrode 108 with respect to the plurality of SES elements 104. The fourth electrode 304 and the fifth electrode 306 may further be substantially coplanar with the plurality of SES elements 104, the first electrode 106, and the second electrode 108. According to a particular example, the fourth electrode 304 and the first electrode 106 may be concentric "C" shaped electrodes. Likewise, the fifth electrode 306 and the second electrode 108 may also be concentric "C" shaped electrodes. In other examples, because the bias to be applied on the first electrode 106 and the second electrode 108 may be the same, the first electrode 106 and the second electrode 108 may be formed of a single ring structure and may thus be a single electrode. For the same reasons, the fourth electrode 304 and the fifth electrode 306 may also be formed of a single ring structure. In this example, the electrodes 106, 108, 304, and 306 of the apparatus 100 may be formed into concentric rings.

In FIG. 3B, currents having negative biases may flow through the first electrode 106 and the second electrode 108. In addition, currents having positive biases may flow through the third electrode 302, the fourth electrode 304, and the fifth electrode 306. As such, the electric field 110 generated by the first electrode 106, the second electrode 108, the third electrode 302, the fourth electrode 304, and the fifth electrode 306 in FIG. 3B may differ from the electric fields 110 depicted as being generated in FIGS. 1B and 3A.

According to an example, the outer electrodes, i.e., the fourth electrode 304 and the fifth electrode 306, may be supplied with an alternating current (AC) voltage while a direct current (DC) bias may be applied between the inner electrodes, i.e., the first electrode 106 and the second electrode 108, and the third electrode 302. In another example, the outer electrodes may be supplied with a DC voltage and the inner electrodes may be supplied with an AC voltage. In a further example, AC voltages may be applied in each of the first electrode 106, the second electrode 108, the fourth electrode 304, and the fifth electrode 306.

According to an example, the fourth electrode 304 and the fifth electrode 306 may operate to ionize particles that flow through the electric fields generated by those electrodes. The ionization of the particles may further enhance deposition of the particles on the SES elements 104. In further examples, additional electrodes may be provided on the substrate 102, for instance, as substantially concentric rings outside of the fourth electrode 304 and the fifth electrode 306.

Figure 4A:
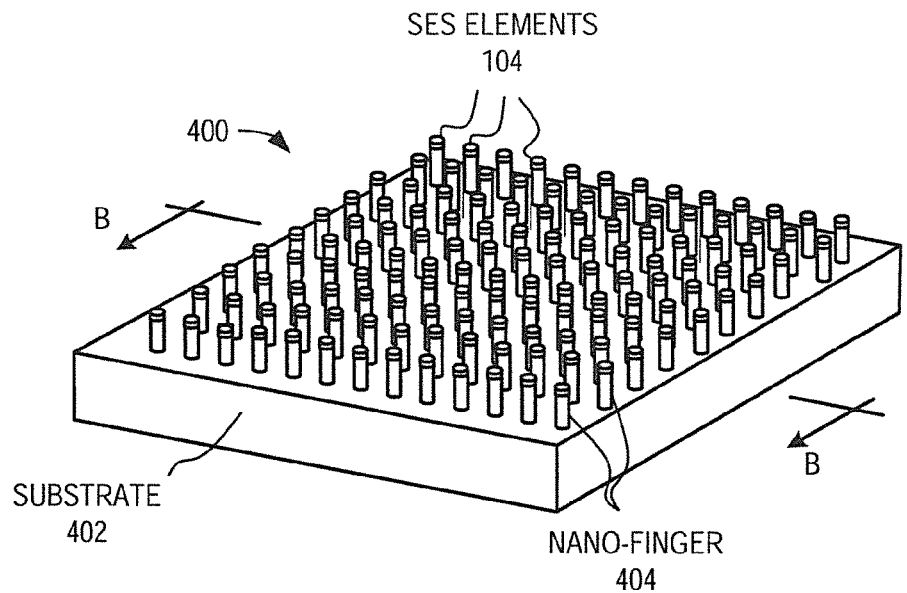
FIG. 4A shows an isometric view of a plurality of SES elements, according to an example of the present disclosure.
Figure 4B:
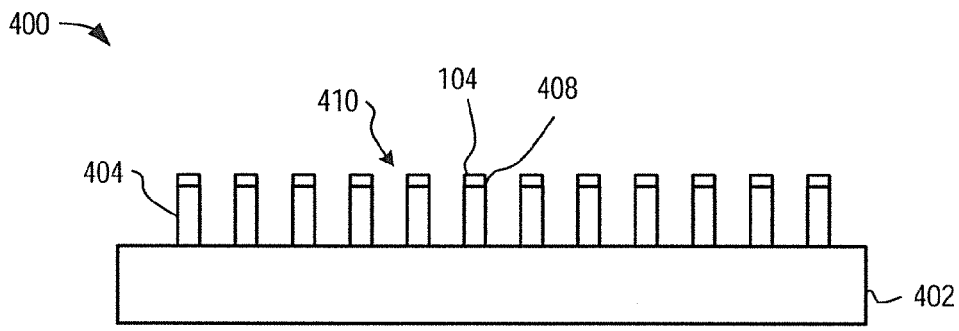
FIGS. 4B and 4C, respectively show cross-sectional views along a line B-B, shown in FIG. 4A, prior to and following collapse of the nano-fingers, according to examples of the present disclosure.
Figure 4C:
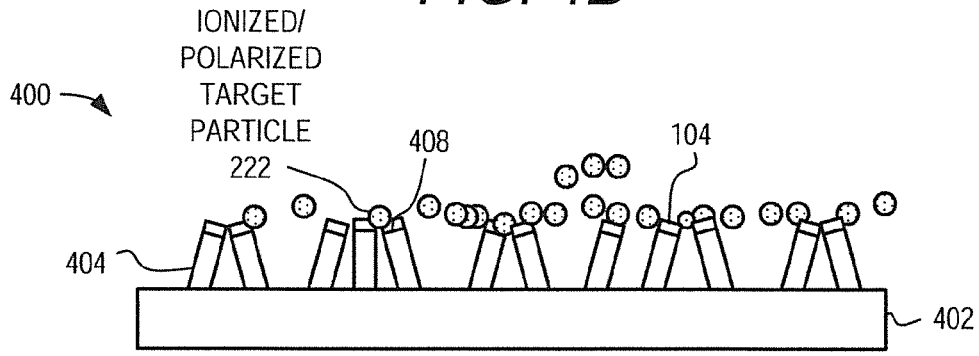

Turning now to FIGS. 4A-4C, there are respectively shown an isometric view and side views of an array 400 of SES elements 104, according to an example. It should be understood that the array 400 depicted in FIGS. 4A-4C may include additional components and that some of the components described herein may be removed and/or modified without departing from a scope of the apparatus 100 disclosed herein. It should also be understood that the components depicted in FIGS. 4A-4C are not drawn to scale and thus, the components may have different relative sizes with respect to each than as shown therein.

Generally speaking, the array 400 of SES elements 104 depicted in FIGS. 4A-4C may be an example of a plurality of SES elements 104 depicted in FIGS. 1A-3B. Particularly, in the array 400, the SES elements 104 may be positioned on the tops of respective nano-fingers 404 that extend above a surface of a substrate 402. The substrate 402 may be formed of any suitable material, such as, silicon, silicon nitride, glass, plastic, polymer, $SiO_2$, $Al_2O_3$, aluminum, etc., or a combination of these materials, etc. The substrate 402 may be the substrate 102 depicted in FIG. 1A or the substrate 402 may be a separate substrate that may be positioned on top of the substrate 102.

According to an example, the nano-fingers 404 may have dimensions that are in the nanometer range, for instance, dimensions that may be less than about 500 nm, and may be formed of a relatively flexible material to enable the nano-fingers 404 to be laterally bendable or collapsible, for instance, to enable tips of the nano-fingers 404 to move toward each other, as discussed in greater detail herein below. Examples of suitable materials for the nano-fingers 404 may include polymer materials, such as, UV-curable or thermal curable imprinting resist, polyalkylacrylate, polysiloxane, polydimethylsiloxane (PDMS) elastomer, polyimide, polyethylene, polypropelene, polyurethane, fluoropolymer, etc., or any combination thereof, metallic materials, such as, gold, silver, aluminum, etc., semiconductor materials, etc., and combinations thereof.

The nano-fingers 404 may be attached to the surface of the substrate 402 through any suitable attachment mechanism. For instance, the nano-fingers 404 may be grown directly on the substrate 402 surface through use of various suitable nano-structure growing techniques. As another example, the nano-fingers 404 may be integrally formed with the substrate 402. In this example, for instance, a portion of the material from which the substrate 402 is fabricated may be etched or otherwise processed to form the nano-fingers 404. In a further example, a separate layer of material may be adhered to the substrate 402 surface and the separate layer of material may be etched or otherwise processed to form the nano-fingers 404. In various examples, the nano-fingers 404 may be fabricated through a nanoimprinting or an embossing process in which a template of relatively rigid pillars is employed in a multi-step imprinting process on a polymer matrix to form the nano-fingers 404. In these examples, a template may be formed through photolithography or other advanced lithography with the desired patterning to arrange the nano-fingers 404 in the predetermined arrangement. More particularly, for instance, the desired patterns may be designed on a mold by any of E-beam lithography, photolithography, laser interference lithography, Focused Ion Beam (FIB), self-assembly of spheres, etc. In addition, the pattern may be transferred onto another substrate, for instance, a silicon, glass, or polymer substrate (polydimethylsiloxane (PDMS), polyimide, polycarbonate, etc.). Various other processes, such as, etching, and various techniques used in the fabrication of micro-electromechanical systems (MEMS) and nano-electromechanical systems (NEMS) may also be used to fabricate the nano-fingers 404.

The nano-fingers 404 have been depicted as having substantially cylindrical cross-sections. It should, however, be understood that the nano-fingers 404 may have other shaped cross-sections, such as, for instance, rectangular, square, triangular, etc. In addition, or alternatively, the nano-fingers 404 may be formed with features, such as, notches, bulges, etc., to substantially cause the nano-fingers 404 to be inclined to collapse in particular directions. Thus, for instance, two or more adjacent nano-fingers 404 may include the features to increase the likelihood that the nano-fingers 404 collapse toward each other. Various manners in which the nano-fingers 404 may be collapsed are described in greater detail herein below.

The array 400 may include a substantially random distribution of nano-fingers 404 or a predetermined configuration of nano-fingers 404. In any regard, according to an example, the nano-fingers 404 may be arranged with respect to each other such that the tips of at least two neighboring nano-fingers 404 are able to be brought into close proximity with each other when the nano-fingers 404 are in a partially collapsed state. By way of particular example, the neighboring nano-fingers 404 may be positioned less than about 100 nanometers apart from each other. According to a particular example, the nano-fingers 404 may be patterned on the substrate 402 such that neighboring ones of the nano-fingers 404 preferentially collapse into predefined geometries, for instance, triangles, squares, pentagons, etc.

Turning now to FIG. 4B, there is shown a cross-sectional view along a line B-B, shown in FIG. 4A, of the array 400, in accordance with an example. As shown therein, each of the tips 408 of the nano-fingers 404 may include a respective SES element 104 disposed thereon. The SES elements 104, which may include metallic nanoparticles, may be deposited onto the tips 408 of the nano-fingers 404 through one of, for instance, physical vapor deposition (PVD), chemical vapor deposition (CVD), sputtering, etc., of metallic material, or self-assembly of pre-synthesized nano-particles.

Although the nano-fingers 404 have been depicted in FIGS. 4A-4B as each extending vertically and at the same heights with respect to each other, it should be understood that some of the nano-fingers 404 may extend at various angles and heights with respect to each other. The differences in angles and/or heights between the nano-fingers 404 may occur, for instance, due to differences arising from manufacturing or growth variances existent in the fabrication of the nano-fingers 404 and the deposition of the SES elements 104 on the nano-fingers 404, etc.

As shown in FIG. 4B, the nano-fingers 404 are in a first position, in which the tips 408 are in a substantially spaced arrangement with respect to each other. The gaps 410 between the tips 408 may be of sufficiently large size to enable a liquid to be positioned in the gaps 410. In addition, the gaps 410 may be of sufficiently small size to enable the tips 408 of at least some of the nano-fingers 404 to be drawn toward each other as the liquid provided in the gaps 410 evaporates, through, for instance, capillary forces applied on the tips 408 as the liquid evaporates.

Turning now to FIG. 4C, there is shown a cross-sectional view along a line B-B, shown in FIG. 4A, of the array 400, following evaporation of the liquid, according to an example. The view depicted in FIG. 4O is identical to the view depicted in FIG. 4B, except that the nano-fingers 404 are depicted in a second position, in which the tips 408 of some of the nano-fingers 404 have been drawn toward with each other. According to an example, the tips 408 of some of the nano-fingers 404 may be in and may remain in relatively close proximity to each other for a period of time due to the capillary forces applied on adjacent ones of the nano-fingers 404 during and following evaporation of the liquid (not shown) in the gaps 410 between the tips 408. In addition, the SES elements 104 on the adjacent tips 408 may bond to each other through, for instance, gold-gold bonding, a binding molecule (not shown), etc.

In one regard, the tips 408 of the nano-fingers 404 may be caused to be drawn toward each other as shown in FIG. 4C to enhance signal emission by the ionized or polarized target particles 222 in the near fields of the SES elements 104 because the relatively small gaps (or no gaps) between the SES elements 104 on the adjacent tips 408 may create "hot spots" having relatively large electric field strengths. According to an example, the nano-fingers 404 may be positioned into the collapsed state depicted in FIG. 4C prior to introduction of a fluid flow 220 (FIG. 2) containing the ionized or polarized target particles 222.

According to another example, the SES elements 104 may be deposited and/or formed directly on the substrate 402. In addition, or alternatively, the SES elements 104 may initially be formed and positioned, for instance, as shown in FIG. 4C, such that the SES elements 104 are either touching each other or are in relatively close proximities to each other and the SES elements 104 may be transferred to another substrate, for instance, the substrate 102.

Figure 5:
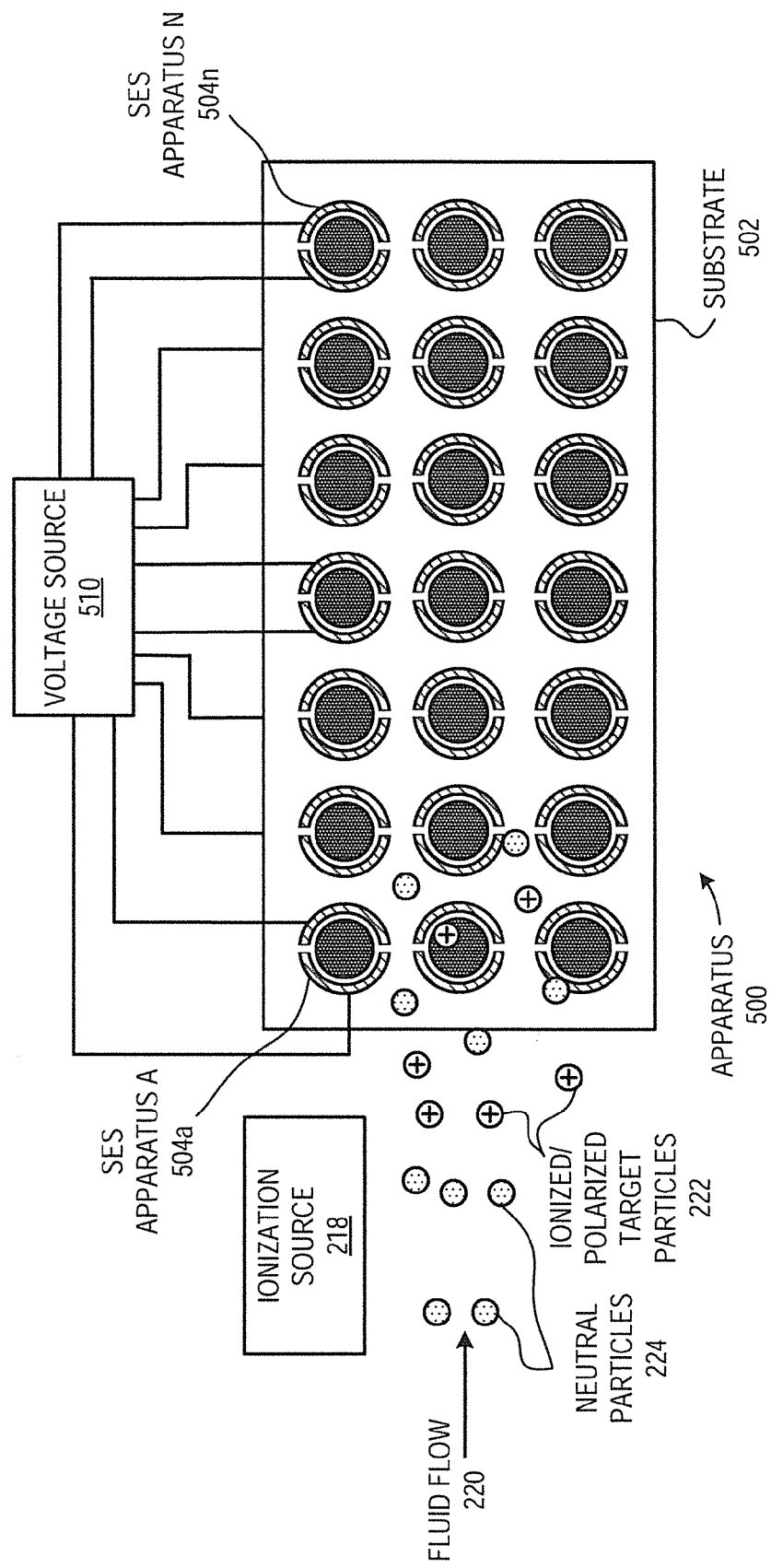
FIG. 5 shows a diagram of an apparatus for performing SES, according to another example of the present disclosure.

Turning now to FIG. 5, there is shown a diagram of an apparatus 500 for performing SES, according to another example. It should be understood that the apparatus 500 depicted in FIG. 5 may include additional components and that some of the components described herein may be removed and/or modified without departing from a scope of the apparatus 500. It should also be understood that the components depicted in FIG. 5 are not drawn to scale and thus, the components may have different relative sizes with respect to each other than as shown therein.

As shown in FIG. 5, the apparatus 500 may be positioned in the path of a fluid flow 220 that contains target particles 222. In addition, the apparatus 500 may be positioned downstream of an ionization source 218 to thus ionize target particles, such that the fluid flow 220 may contain both ionized or polarized target particles 222 and neutral particles 224. In one example, the apparatus 500 may be used in a SES system 200, for instance, as shown in FIG. 2.

The apparatus 500 may include a substrate 502 on which is positioned a plurality of SES apparatuses 504a-504n, in which the variable "n" represents an integer equal to or greater than one. The substrate 502 may include any of the materials discussed above with respect to the substrate 102. In addition, the SES apparatuses 504a-504n may be arranged in a two-dimensional array. Moreover, each of the SES apparatuses 504a-504n may have a configuration similar or identical, except for the substrate 102, to any of the apparatuses 100 depicted in FIGS. 1A-3B.

Also shown in FIG. 5 is a voltage source 510 that may supply the first electrodes 106 and the second electrodes 108 of the SES apparatuses 504a-504n with oppositely biased voltages to generate respective electric fields 110 near the SES elements 104 as discussed above. As also discussed above with respect to the examples depicted in FIGS. 3A and 3B, the SES apparatuses 504a-504n may include additional electrodes, for instance, any of the third electrode 302, the fourth electrode 304, and the fifth electrode 306. In those examples, the voltage source 510 may also supply power to the additional electrodes in manners as discussed above.

The voltage source 510 is depicted in FIG. 5 as being connected to three of the SES apparatuses 504a-504n for purposes of simplicity. It should therefore be understood that the voltage source 510 may be connected to the electrodes of each of the SES apparatuses 504a-504n. Alternatively, a plurality of voltage sources (not shown) may supply voltages to each of the SES apparatuses 504a-504n or groups of SES apparatuses 504a-504n. In addition, the voltages applied to the SES apparatuses 504a-504n may be individually controlled. In this regard, electric fields 110 may selectively be generated on the SES apparatuses 504a-504n to attract ionized or polarized target particles 222 to the selected SES apparatuses 504a-504n.

In addition, or alternatively, electric fields having different strengths may be generated in at least some of the SES apparatuses 504a-504n with respect to each other. Thus, for instance, some of the SES apparatuses 504a-504n may include electrodes that are relatively larger than the electrodes on other ones of the SES apparatuses 504a-504n. In addition, or alternatively, the voltage source 510 may supply greater voltage levels to the electrodes of some of the SES apparatuses 504a-504n as compared with other ones of the SES apparatuses 504a-504n. As a further example, some of the SES apparatuses 504a-504n may have a different number of electrodes as compared with other ones of the SES apparatuses 504a-504n. In this example, some of the SES apparatuses 504a-504n may have first and second electrodes 106 and 108 as shown in FIGS. 1A and 1B while other ones of the SES apparatuses 504a-504n may also have the third electrodes 302 as shown in FIG. 3A and/or the fourth and fifth electrodes 304 and 306 as shown in FIG. 3B. As a yet further example, the electrodes of some of the SES apparatuses 504a-504n may be spaced at different distances from their respective SES elements 104 as compared with other ones of the SES apparatuses 504a-504n. According to a further example, some or all of the SES apparatuses 504a-504n may ionize target particles contained in a fluid flow to enhance deposition of the target particles onto the SES elements 104 of the SES apparatuses 504a-504n. In this example, the ionization source 218 may not be required.

Figure 6:
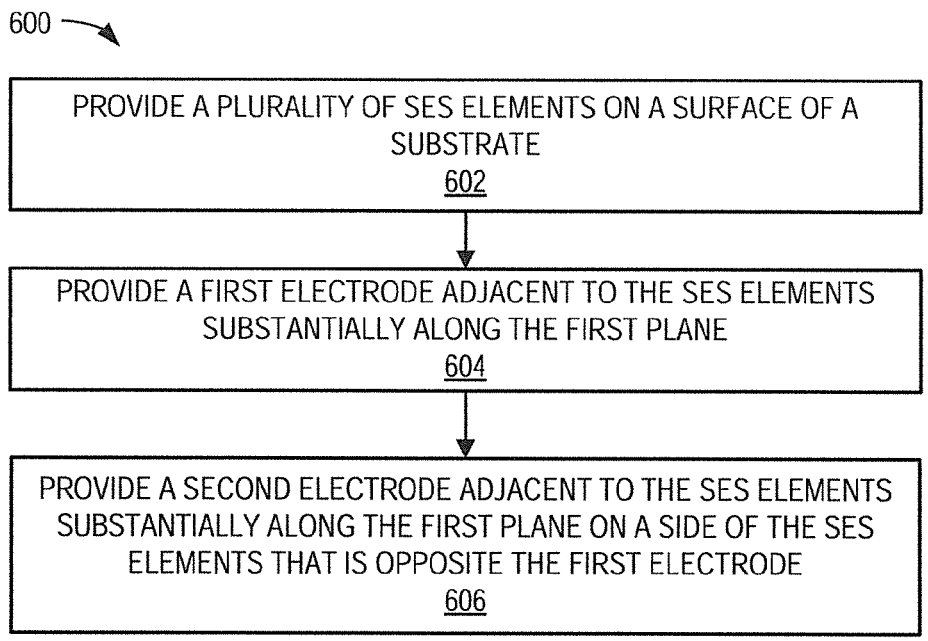
FIG. 6 shows a flow diagram of a method for fabricating an apparatus for performing spectroscopy, according to an example of the present disclosure.

Turning now to FIG. 6, there is shown a flow diagram of a method 600 for fabricating an apparatus 100 for performing spectroscopy, according to an example. It should be understood that the method 600 depicted in FIG. 6 may include additional processes and that some of the processes described herein may be removed and/or modified without departing from a scope of the method 600. In addition, although particular reference is made herein to the apparatus 100 as being fabricated through implementation of the method 600, it should be understood that the method 600 may be implemented to fabricate a differently configured apparatus without departing from a scope of the method 600.

At block 602, a plurality of SES elements 104 may be provided on a surface of a substrate 102, in which the plurality of SES elements 104 may extend substantially along a first plane on the surface of the substrate 102. The SES elements 104 may be provided on the surface of the substrate 102 through deposition or other formation process of the SES elements 104. By way of particular example, the SES elements 104 may be formed on tips of nano-fingers 404 as discussed above with respect to FIGS. 4A-4C.

At block 604, a first electrode 106 may be provided, in which the first electrode 106 may be positioned adjacent to the plurality of SES elements 104 substantially along the first plane. The first electrode 106 may be provided on the surface of the substrate 102 through any suitable electrode fabrication process and/or the first electrode 106 may be laid on the substrate 102 following fabrication of the first electrode 106. For instance, the first electrode 106 may be provided on the surface through suitable lithographic techniques, through suitable metal deposition techniques, etc. In addition, the first electrode 106 may be provided on the substrate to have any shape as discussed above.

At block 606, a second electrode 108 may be provided, in which the second electrode 108 is positioned adjacent to the SES elements 104 substantially along the first plane and on a side of the SES elements 104 that is opposite the first electrode 106. The second electrode 108 may be provided on the substrate 102 in any of the manners discussed above with respect to the first electrode 106. As also discussed above, the first electrode 106 and the second electrode 108 may generate an electric field around the plurality of SES elements 104 when voltages are applied through the first electrode 106 and the second electrode 108.

The method 600 may include additional operations. For instance, the method 600 may include the providing of a third electrode 302 as shown in FIG. 3A. The method 600 may also include the providing of the fourth electrode 304 and the fifth electrode 306 as shown in FIG. 3B.

Figure 7:
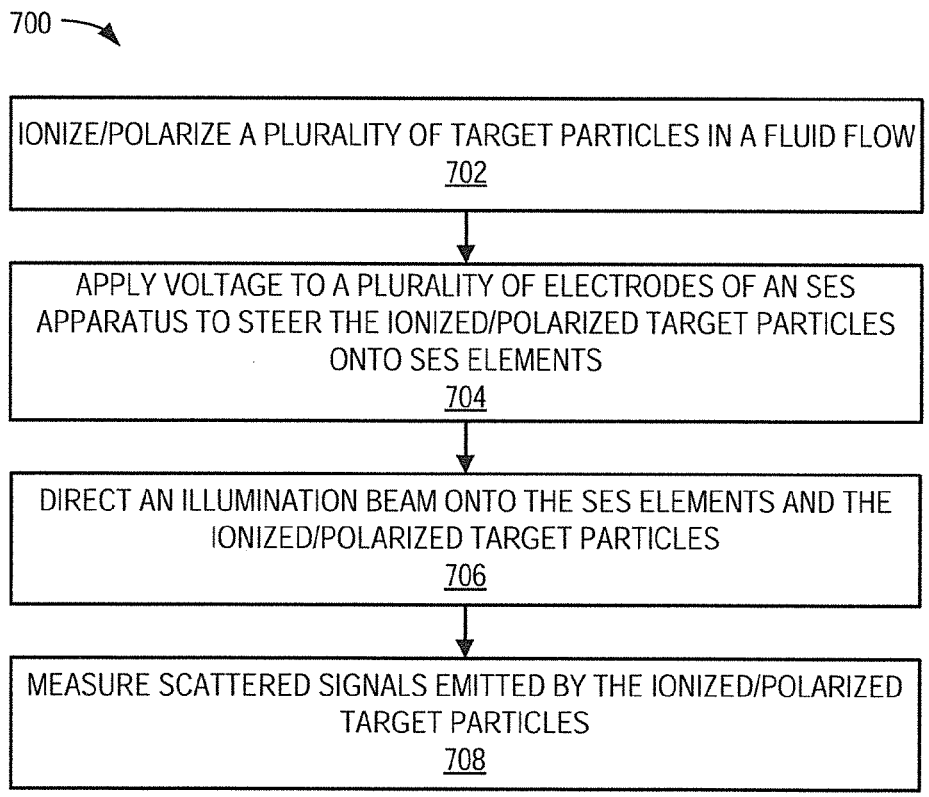
FIG. 7 shows a flow diagram of a method for using an apparatus for performing spectroscopy, according to an example of the present disclosure.

Turning now to FIG. 7, there is shown a flow diagram of a method 700 for using an apparatus 100 for performing spectroscopy, according to an example. It should be understood that the method 700 depicted in FIG. 7 may include additional processes and that some of the processes described herein may be removed and/or modified without departing from a scope of the method 700. In addition, although particular reference is made herein to the apparatus 100 as being used in the method 700, it should be understood that the method 700 may use a differently configured apparatus without departing from a scope of the method 700.

At block 702, a plurality of target particles 222 (FIG. 2) in a fluid flow 220 may be ionized or polarized. As discussed above, an ionization source 218 may ionize the target particles 222. In addition, or alternatively, outer electrodes 304, 306 (FIG. 3B) positioned outside of the first electrode 106 and the second electrode 108 may ionize the target particles 222.

At block 704, a voltage to the first electrode 106 and the second electrode 108 may be applied to generate an electric field 110 over the plurality of SES elements 104 to steer the plurality of ionized or polarized target particles 222 onto the plurality of SES elements 104. As discussed above with respect to FIG. 1B, a voltage having positive bias may be applied through one of the first and second electrodes 106, 108 and a voltage having a negative bias may be applied through the other one of the first and second electrodes 106, 108. In addition, as discussed above with respect to FIG. 5, voltages may be applied to the electrodes of multiple SES apparatuses 504a-504n in a controlled manner.

At block 706, an illumination beam 206 may be directed onto the plurality of SES elements 104 and the ionized or polarized target particles 222 to cause the ionized or polarized target particles 222 to emit scattered signals 212. As discussed above, the SES elements 104 generally enhance emission of the scattered signals 212 from the ionized or polarized target particles 222 that are in contact with or in relatively close proximity to the SES elements 104. In addition, the scattered signals 212 may be directed to a spectrometer 214.

At block 708, the scattered signals 212 emitted by the ionized or polarized target particles 222 may be measured. The scattered signals 212 may be measured by the spectrometer 214 as discussed above with respect to FIG. 2.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for performing spectroscopy, the apparatus comprising:
   a substrate having a surface;
   a plurality of surface-enhanced spectroscopy (SES) elements positioned substantially along a first plane on the surface of the substrate;
   a first electrode positioned adjacent to the plurality of SES elements substantially along the first plane;
   a second electrode positioned adjacent to the plurality of SES elements substantially along the first plane and on a side of the plurality of SES elements that is opposite the first electrode, wherein the first electrode and the second electrode are to generate an electric field around the plurality of SES elements when voltages are applied through the first electrode and the second electrode; and
   a third electrode positioned beneath the plurality of SES elements, wherein the first electrode and the second electrode are to have a common bias and the third electrode is to have a bias that is opposite the common bias.

2. The apparatus according to claim 1, wherein the first electrode and the second electrode are positioned on the surface of the substrate.

3. The apparatus according to claim 1, further comprising:
   a fourth electrode positioned outside of the first electrode with respect to the plurality of SES elements; and
   a fifth electrode positioned outside of the second electrode with respect to the plurality of SES elements, wherein fourth electrode and the fifth electrode are to have a bias that is opposite the common bias.

4. The apparatus according to claim 3, wherein the first electrode, the second electrode, the fourth electrode, and the fifth electrode comprise at least one of semicircular and ring shapes.

5. The apparatus according to claim 1, further comprising:
   a plurality of nano-fingers extending from the surface of the substrate, wherein the plurality of SES elements are positioned on tips of the plurality of nano-fingers.

6. The apparatus according to claim 5, wherein the plurality of nano-fingers are collapsed onto adjacent ones of the plurality of nano-fingers such that tips of at least some of the adjacent nano-fingers are in close proximities with respect to each other and that the plurality of SES elements on the tips of at least some of the adjacent nano-fingers are in contact with each other.

7. An apparatus for performing spectroscopy, said system comprising:

a substrate having a surface;
a plurality of surface-enhanced spectroscopy (SES) apparatuses positioned on the surface, each of the plurality of SES apparatuses including,
    a plurality of SES elements positioned substantially along a first plane on the surface of the substrate;
    a first electrode positioned adjacent to the plurality of SES elements substantially along the first plane; and
    a second electrode positioned adjacent to the plurality of SES elements substantially along the first plane and on a side of the plurality of SES elements that is opposite the first electrode, wherein the first electrode and the second electrode are to generate an electric field around the plurality of SES elements when voltages are applied through the first electrode and the second electrode; and
    wherein a first SES apparatus of the plurality of SES apparatuses is to generate an electric field having a different strength as compared with a second SES apparatus of the plurality of SES apparatuses.

8. The apparatus according to claim 7, wherein the plurality of SES apparatuses are positioned on the surface in a two-dimensional array.

9. The apparatus according to claim 7, wherein each of the plurality of SES apparatuses further comprises a plurality of nano-fingers extending from the surface of the substrate, wherein the SES elements are positioned on tips of the plurality of nano-fingers.

10. The apparatus according to claim 9, wherein the plurality of nano-fingers are collapsed onto adjacent ones of the plurality of nano-fingers such that tips of the adjacent nano-fingers are in close proximities with respect to each other such that the SES elements on the tips of adjacent nano-fingers are in contact with each other.

11. A method for fabricating a spectroscopy apparatus, said method comprising:
    providing a plurality of surface-enhanced spectroscopy (SES) elements on a surface of a substrate substantially along a first plane;
    providing a first electrode adjacent to the plurality of SES elements substantially along the first plane;
    providing a second electrode adjacent to the plurality of SES elements substantially along the first plane and on a side of the plurality of SES elements that is opposite the first electrode, wherein the first electrode and the second electrode are to generate an electric field around the plurality of SES elements when voltages are applied through the first electrode and the second electrode; and
    providing a third electrode positioned beneath the plurality of SES elements, wherein the first electrode and the second electrode are to have a common bias and the third electrode is to have a bias that is opposite the common bias.

12. The method according to claim 11, further comprising:
    providing a fourth electrode outside of the first electrode with respect to the plurality of SES elements; and
    providing a fifth electrode outside of the second electrode with respect to the plurality of SES elements.

\* \* \* \* \*